United States Patent
Li et al.

(10) Patent No.: US 8,570,506 B2
(45) Date of Patent: Oct. 29, 2013

(54) SYSTEM FOR INSPECTING DEFECTS OF PANEL DEVICE

(75) Inventors: Jung-Yu Li, Taipei County (TW); Shih-Pu Chen, Hsinchu (TW); Yi-Ping Lin, Changhua County (TW); Lian-Yi Cho, Miaoli County (TW)

(73) Assignee: Industrial Technology Research Institute, Hsinchu (TW)

( * ) Notice: Subject to any disclaimer, the term of this patent is extended or adjusted under 35 U.S.C. 154(b) by 1159 days.

(21) Appl. No.: 12/144,648

(22) Filed: Jun. 24, 2008

(65) Prior Publication Data

US 2009/0244527 A1    Oct. 1, 2009

(30) Foreign Application Priority Data

Mar. 28, 2008   (TW) ................................ 97111527 A

(51) Int. Cl.
*G01N 21/00*   (2006.01)

(52) U.S. Cl.
USPC ....................................................... 356/237.2

(58) Field of Classification Search
USPC ....................................................... 356/237.2
See application file for complete search history.

(56) References Cited

U.S. PATENT DOCUMENTS

| | | | |
|---|---|---|---|
| 4,236,096 A | | 11/1980 | Tiemann |
| 4,855,646 A | * | 8/1989 | Peckitt et al. .................. 315/175 |
| 5,633,504 A | * | 5/1997 | Collins et al. .............. 250/461.1 |
| 6,791,682 B2 | * | 9/2004 | Kobayashi ................. 356/239.1 |
| 6,891,612 B1 | * | 5/2005 | Koike et al. ................. 356/237.6 |
| 6,897,606 B2 | * | 5/2005 | Deguchi ......................... 313/496 |
| 7,134,761 B2 | * | 11/2006 | Francke .......................... 362/84 |
| 7,554,254 B2 | * | 6/2009 | Lee et al. ....................... 313/485 |
| 7,834,540 B2 | * | 11/2010 | Lee et al. ....................... 313/504 |
| 2002/0105638 A1 | * | 8/2002 | Kobayashi ................. 356/239.1 |
| 2004/0135492 A1 | * | 7/2004 | Deguchi ......................... 313/496 |
| 2005/0062413 A1 | * | 3/2005 | Francke ......................... 313/512 |
| 2008/0143238 A1 | * | 6/2008 | Li et al. ......................... 313/491 |
| 2008/0214085 A1 | * | 9/2008 | Lee et al. ........................ 445/26 |

FOREIGN PATENT DOCUMENTS

| | | |
|---|---|---|
| CN | 1354362 | 6/2002 |
| CN | 1618113 | 5/2005 |
| EP | 1691585 A1 * | 8/2006 |
| EP | 1936661 A1 * | 6/2008 |
| TW | 571079 | 1/2004 |
| TW | I254339 | 5/2006 |
| WO | WO 03054902 A1 * | 7/2003 |

OTHER PUBLICATIONS

"Office Action of Taiwan Counterpart Application", issued on Feb. 4, 2012, p. 1-6, in which the listed references were cited.

* cited by examiner

*Primary Examiner* — Roy M Punnoose
(74) *Attorney, Agent, or Firm* — Jianq Chyun IP Office

(57) ABSTRACT

System for inspecting defects of panel device includes a to-be-inspected device, a platform for holding the to-be-inspected device, a power unit, and a light source apparatus. The light source apparatus is controlled by the power unit to provide an inspection light to the to-be-inspected device for inspecting whether or not having defects. The light source apparatus includes a cathode structure, an anode structure, a fluorescent layer, and a low-pressure gas layer. The fluorescent layer is located between the cathode structure and the anode structure. The low-pressure gas layer is filled between the cathode structure and the anode structure, for inducing the cathode to emit electrons uniformly. The low-pressure gas layer has an electron mean free path, allowing at least enough electrons to directly hit the fluorescent layer under an operating voltage.

22 Claims, 6 Drawing Sheets

(a)

(b)

SYSTEM FOR INSPECTING DEFECTS OF PANEL DEVICE

CROSS-REFERENCE TO RELATED APPLICATION

This application claims the priority benefit of Taiwan application serial no. 97111527, filed on Mar. 28, 2008. The entirety of the above-mentioned patent application is hereby incorporated by reference herein and made a part of this specification.

BACKGROUND OF THE INVENTION

1. Field of the Invention

The present invention generally relates to a system for inspecting defects of a panel device, capable of, for example, inspecting the optically detected defects on a panel device.

2. Description of Related Art

Defect inspection of devices is a necessary process for reducing performance defects of final products. For example, during the manufacturing process, the elements of the display panel or the transparent elements may have defects on their surfaces or in their inner parts. The defects include various defects that are inspected by light beam, for example, foreign particles adhered on the surfaces, surface cracks, and the like or foreign particles, holes, or cracks of the inner parts, and the like. The defects may also be, for example, pin holes, foreign matters, white spots, or the like. These defects can be inspected by a light passing through the devices or a light reflected by the surfaces of the devices.

FIGS. 1A and 1B are schematic views of a conventional device inspection mechanism. Referring to FIG. 1A, a light source 100 produces an inspection light. The inspection light passes through a transparent or semi-transparent to-be-inspected device 102, for inspecting defects of products. For example, an inspector 104 observes the changes of the transmitted light, so as to determine whether there are defects or not. Referring to FIG. 1B, the inspection mechanism is used to inspect whether the surface of to-be-inspected device has defects.

Currently, a white-light box is used for inspecting defects of products available on the market, which is mainly constituted by fluorescent lamps. The white-light box works on the principle of the light diffusion for producing a visual expansion effect after the light passes through the small holes, such that the defects look larger than its actual size. By the use of these characteristics, the defects such as pin holes, foreign matters, or white spots on the product surface can be inspected. Therefore, the white-light box becomes an important quality inspection tool used in the production lines of factories in many industries. For example, the adhesion of liquid crystal display or the color filter needs the quality control inspection.

The light box manufactured by the fluorescent lamps has disadvantages of bulk volume and large thickness, and needs a semi-transparent diffuser and a reflective manner to uniform the light beam. However, the diffuser may attenuate the intensity of the light, so the brightness of the fluorescent lamp must be increased for compensation, which is power consuming and increases the manufacturing cost. In addition, since the physical characteristics of the fluorescent lamps can only achieve a multi-level dimming, the generated light color is limited to the white light and the day light, and thus the adjustment scope is limited.

SUMMARY OF THE INVENTION

Accordingly, the present invention is directed to a system for inspecting defects of a panel device, which uses improved light source apparatus to at least improve the performance of inspecting defects of the device.

The present invention provides a system for inspecting defects of a panel device, which includes a to-be-inspected device, a power unit, and a light source apparatus. The light source apparatus holds the to-be-inspected device, and is controlled by the power unit to provide an inspection light to the to-be-inspected device for inspecting whether or not having defects. The light source apparatus includes a cathode structure, an anode structure, a fluorescent layer, and a low-pressure gas layer. The fluorescent layer is located between the cathode structure and the anode structure. The low-pressure gas layer is filled between the cathode structure and the anode structure, for inducing the cathode to emit electrons uniformly. The low-pressure gas layer has an electron mean free path, allowing at least enough electrons to directly hit the fluorescent layer under an operating voltage.

The present invention provides a system for inspecting defects of a panel device, which includes a to-be-inspected device, a platform for holding the to-be-inspected device, a power unit, and a light source apparatus. The light source apparatus is controlled by the power unit to provide an inspection light to the to-be-inspected device for inspecting whether or not having defects. The light source apparatus includes a cathode structure, an anode structure, a fluorescent layer, and a low-pressure gas layer. The fluorescent layer is located between the cathode structure and the anode structure. The low-pressure gas layer is filled between the cathode structure and the anode structure, for inducing the cathode to emit electrons uniformly. The low-pressure gas layer has an electron mean free path, allowing at least enough electrons to directly hit the fluorescent layer under an operating voltage.

In order to the make aforementioned and other objects, features and advantages of the present invention comprehensible, preferred embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1A:
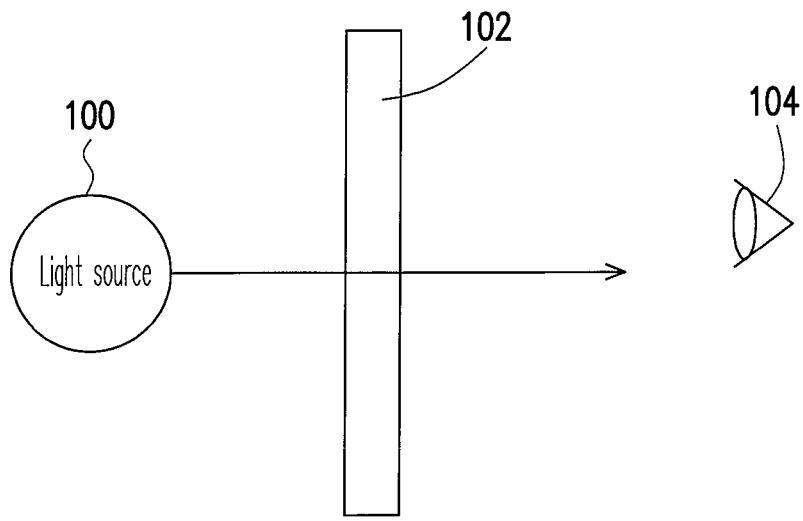
FIGS. 1A and 1B are schematic views of a conventional device inspection mechanism.
Figure 1B:
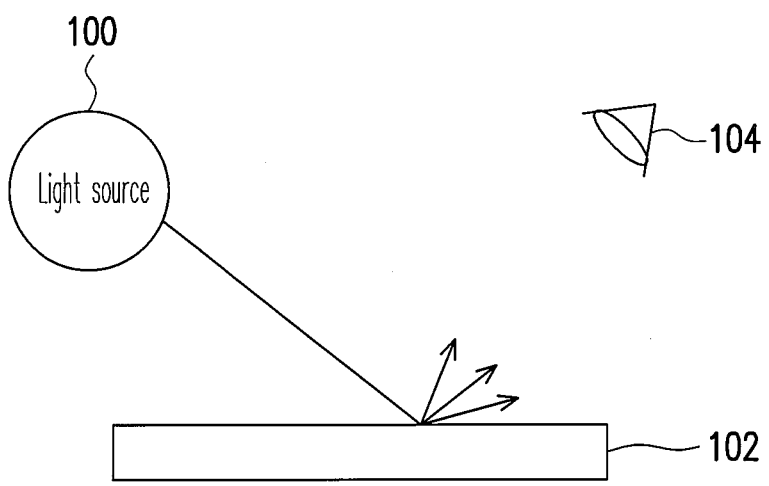

Reference will now be made in detail to the present embodiments of the invention, examples of which are illustrated in the accompanying drawings. Wherever possible, the same reference numbers are used in the drawings and the description to refer to the same or like parts.

The present invention is, for example, applicable to a flat light source equipment for product inspection in the production lines. The present invention provides a flat electron emission lamp (FEEL) serving as the inspection light source, which can be used as the light source of the inspection light box. Here, the flat light source refers to the surface light source, and the surface may be curving surface or planar surface as required.

Figure 8:
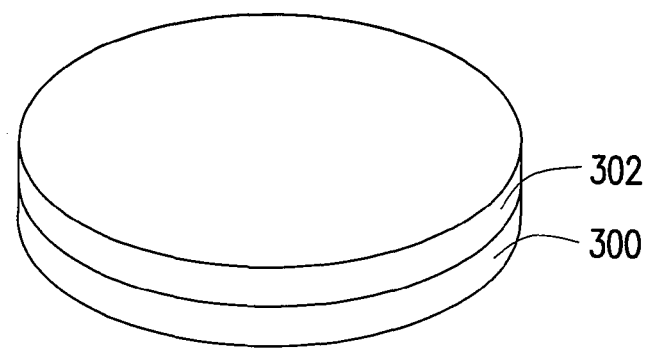
FIG. 8 is a schematic view of profiles of a light source apparatus and a power unit according to an embodiment of the present invention.
Figure 8:
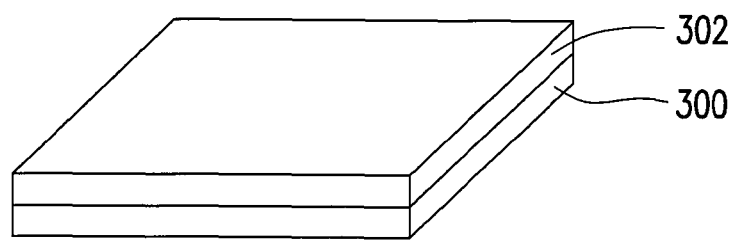
Figure 9:
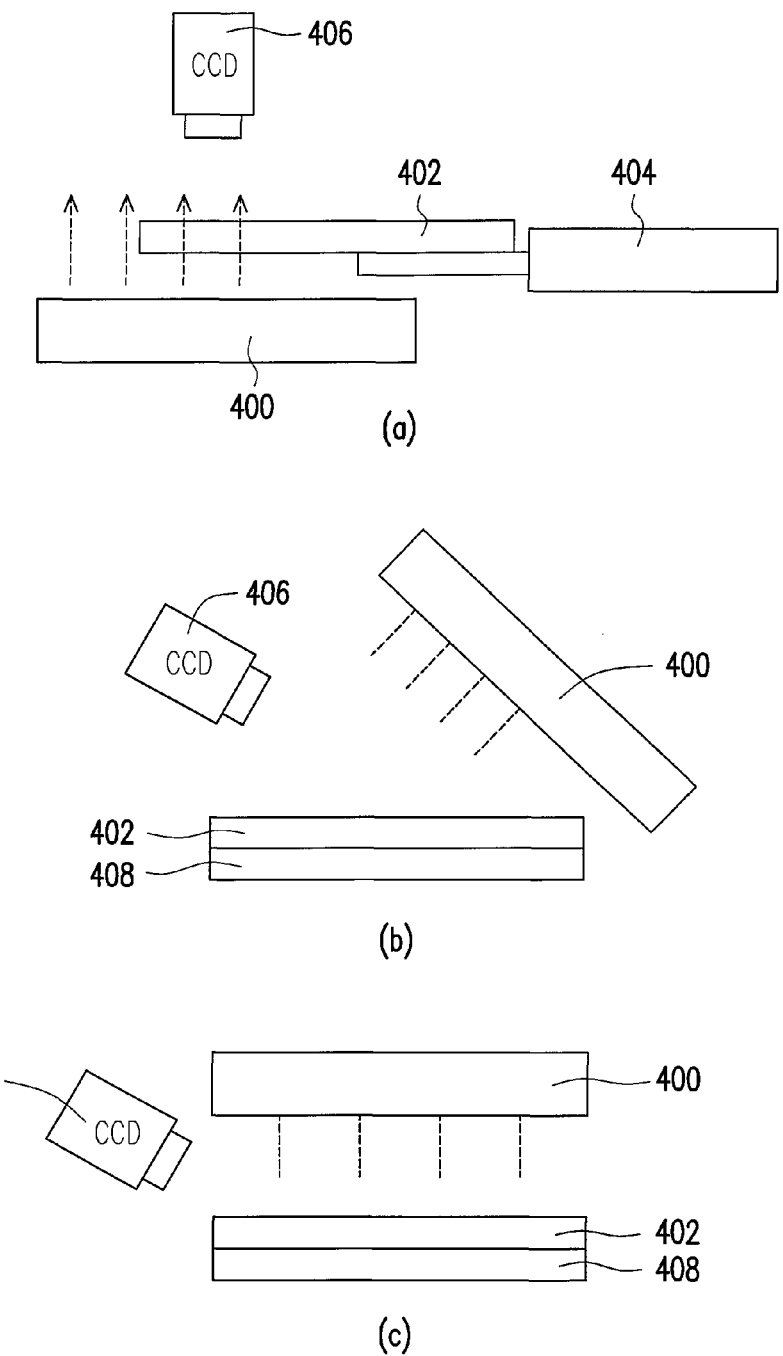
FIG. 9 is a schematic view of a system for inspecting defects of a panel device according to an embodiment of the present invention.

The light source of the inspection light box is the FEEL instead since the FEEL is a flat light source and does not need the diffuser, thereby reducing the light loss. In addition, the light source apparatus of the present invention may be fabricated into light sources of various sizes and shapes, for example, rectangular or round as shown in FIG. 8 according to actual requirements. The reflecting mechanism only needs the flat reflective surface, so the entire inspection device can be fabricated thinner, and the complete set of system has more flexibility in cooperating with the arrangement of various equipments in the production lines or the environment, as shown in FIG. 9.

The light source apparatus of the system for inspecting defects of a panel device of the present invention will be illustrated in the following embodiments, but it should not be considered as the limitations to the present invention, and appropriate changes and combinations may be made to the following embodiments.

Figure 2:
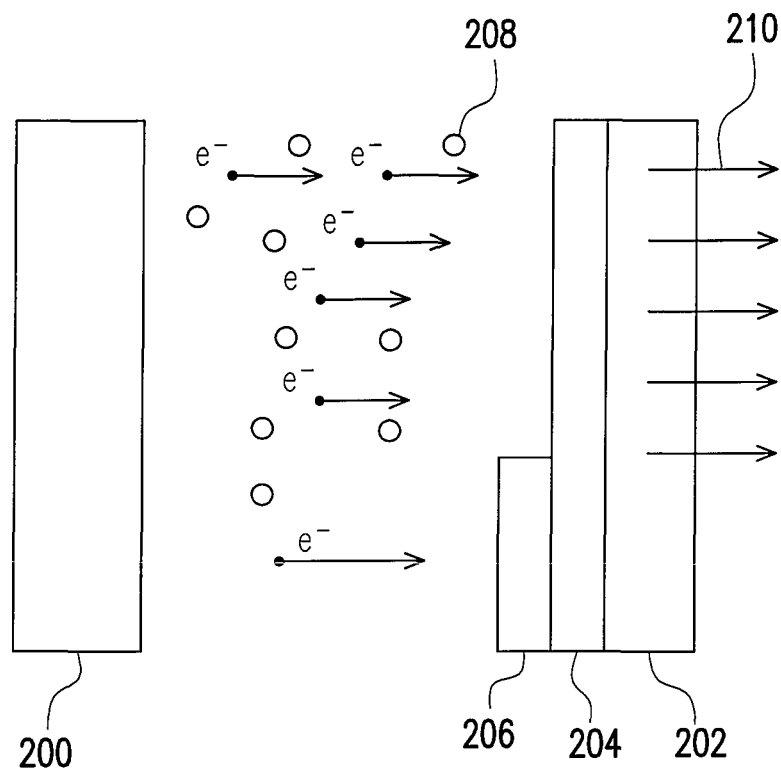
FIG. 2 is a schematic cross-sectional view of a light-emitting mechanism according to an embodiment of the present invention.

FIG. 2 is a schematic cross-sectional view of a light-emitting mechanism according to an embodiment of the present invention. Referring to FIG. 2, in an embodiment, the light source apparatus includes a cathode structure layer 200 and an anode structure layer 202. Here, the cathode structure layer 200 and the anode structure layer 202 of the light source apparatus basically include a substrate and an electrode layer on the substrate respectively, and the actual structure can be changed according to the actual design. In addition, other elements such as power control circuit are known to those of ordinary skill in the art, and can be changed according to the actual design, so the details will not be described herein. The structures of the cathode structure layer 200 and the anode structure layer 202 are, for example, surface structures in this embodiment. The light-emitting mechanism of the present invention easily matches with the design of the electrode structure, and can achieve a large-area surface light-emitting performance, and provide uniform light source intensity. Therefore, the light-emitting mechanism of the present invention is adapted to serve as the inspection light source of the device.

A fluorescent layer 204 is disposed between the cathode structure layer 200 and the anode structure layer 202, and generally, is disposed, for example, on the anode structure layer 202. In addition, an insulating transparent layer 206, for example, quartz or glass, may be disposed for preventing the electrons hitting the fluorescent powder and defining the light-emitting region. A low-pressure gas 208 is filled between the cathode structure layer 200 and the anode structure layer 202, for example in a range of $10$-$10^{-3}$ torrs. The electron mean free path of the low-pressure gas 208 is approximately larger than 1 mm. Definitely, the gas is enclosed in a space in a conventional manner, and the details will not be described herein. In addition, the voltage output/input device may be achieved by the conventional art, and the details will not be described herein.

It should be noted that the filled gas is used to induce the cathode to emit electrons uniformly, so the selected gas is preferably the one that can be easily ionized, and may also be any other gases. The used gas is, for example, atmospheric air, $N_2$, $O_2$, He, Ne, Ar, Kr, Xe, $H_2$, $CO_2$, etc. The filled gas is medium vacuum, so the electrons mean free path thereof is large enough, allowing enough electrons to be accelerated by the electric field to have enough energy to hit the material of the fluorescent layer 204, so as to emit a desired light.

In other words, the present invention uses a gas discharge mechanism to produce enough secondary electrons and ionized electrons, and a field emission mechanism allowing the electrons to hit the fluorescent layer 204, so as to produce the desired light. The wavelength of the light differs according to different materials of the fluorescent layer 204. Further, the fluorescent layer 204 is not limited to be a single layer structure or a monochromatic light. For example, the fluorescent layer 204 may be a lamination structure or a mixed layer structure of the multi-layer structure, capable of mixing the color lights emitted by different fluorescent layers into another color light. Alternatively, the fluorescent layers of different color lights may be arranged adjacent to each other horizontally, instead of being laminated. The above changes fall within the scope of the fluorescent layer design.

Figure 3:
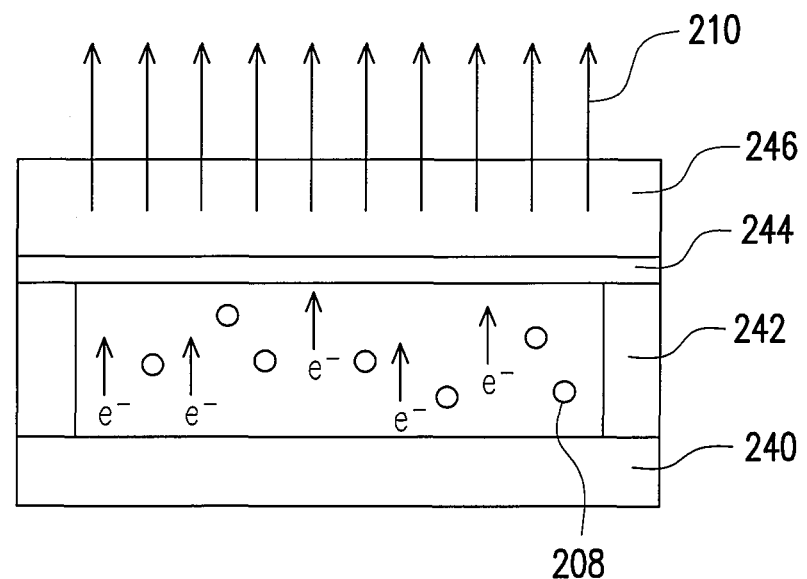
FIG. 3 is a schematic cross-sectional view of a surface light-emitting apparatus according to an embodiment of the present invention.

FIG. 3 is a schematic cross-sectional view of a surface light-emitting apparatus according to an embodiment of the present invention. Referring to FIG. 3, for example, the surface light-emitting apparatus includes a cathode structure 240 and an anode structure 246. The fluorescent layer 244 is disposed between the cathode structure 240 and the anode structure 246, and preferably on a surface of the anode structure 246. The cathode structure 240 and the anode structure 246 are separated for a distance by a sidewall structure 242, and at the same time, a space is enclosed for the low-pressure gas 208 to fill in. By the use of the above mechanism, a proper operating voltage is applied on the cathode structure 240 and the anode structure 246 to generate a desired electric field, so as to accelerate the electrons to hit the fluorescent layer 244. Therefore, the desired light source 210 is emitted from the anode structure 246. Generally speaking, the low-pressure gas 208 is at a preset air pressure, and the intensity of the light is, for example, substantially in a positive direct proportion to the operating voltage range.

The anode structure 246 is, for example, a light-transmissive material. The anode conductive material is, for example, ITO. The supporting substrate is, for example, quartz or glass. The light-transmissive material allows the generated light to come out. A light-reflective metal material may also be adopted instead of the light-transmissive material according to different light-exit surfaces depending on the actual design. Further, for example, in order to prevent the light leakage, a reflective layer may also be disposed on a surface of the cathode structure 240, such that the cathode structure 240 has the reflective function. The cathode material of the cathode structure 240 may be a light-reflective metal, and the light-exit surface is indicated by arrows. If the cathode material of the cathode structure 240 is the conductive transparent material, a reflective surface or a reflective layer may be added to cooperate with the substrate. In other words, the cathode structure 240 may be designed to have the light reflective function, for improving the use efficiency of the light, depending on the actual requirements.

Additionally, the surface of the cathode structure may be a metal, a carbon nano material, zinc oxide, or other discharge materials. The anode material of the anode structure is, for example, a transparent conductive material, for example, ITO, FTO, TCO, etc.

Additionally, a secondary electron source material may also be disposed on the surface of the cathode structure of the light source apparatus, so as to increase the generation of electrons. The secondary electron source material is, for example, MgO, $SiO_2$, $Tb_2O_3$, $La_2O_3$, $CeO_2$, etc. In addition, the fluorescent material can emit the visible light with the desired wavelength according to different materials.

Figure 4A:
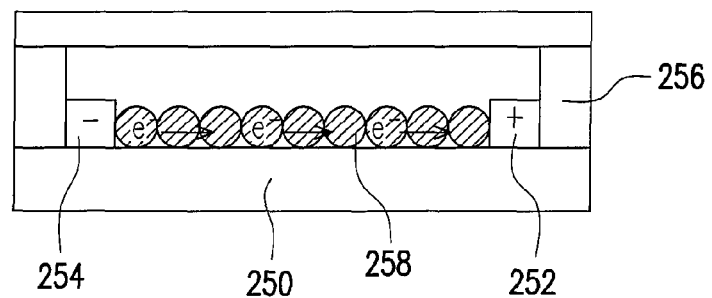
FIGS. 4A and 4B are schematic cross-sectional views of a surface light-emitting apparatus according to another embodiment of the present invention.

FIG. 4A is a schematic cross-sectional view of a surface light-emitting apparatus according to another embodiment of the present invention. Referring to FIG. 4A, based on the same design principle, a closed space may be formed by upper and lower substrates 250 and the sidewall structure 256, for the desired low-pressure gas to fill in. However, in this embodiment, both the anode structure 252 and the cathode structure 254 are disposed on the lower substrate 250, thus forming a transverse electric field. In this structure, the fluorescent layer 258 is also disposed on the portion of the lower substrate 250 between the anode structure 252 and the cathode structure 254. The fluorescent layer 258 is, for example, designed to be spherical surface or column surface monomers adjacent to and in contact with one another, which are distributed on the lower substrate 250 between the anode structure 252 and the cathode structure 254. Additionally, in order to make the generated light emit from a single side, for example, the lower substrate 250 may also be designed to have the reflective function.

Figure 4B:
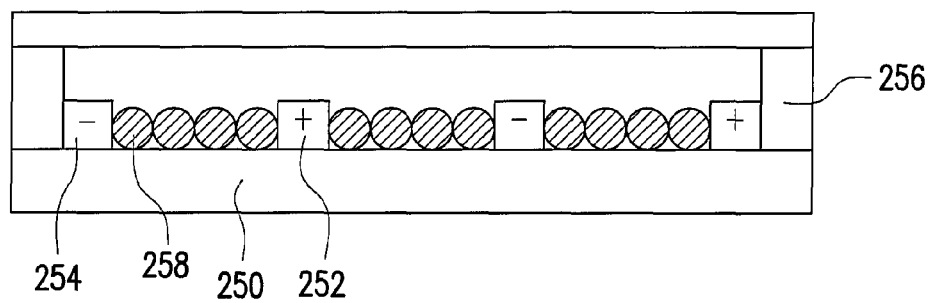

In addition, the structure of FIG. 4A may be further changed. FIG. 4B is a schematic cross-sectional view of a surface light-emitting apparatus according to another embodiment of the present invention. Referring to FIG. 4B, a plurality of light regions may be formed by the arrangement of a plurality of anode structures 252 and cathode structures 254. The light-emitting regions can emit lights having the same frequency range according to the actual requirements, for example, ultraviolet lights, infrared lights, white lights, or other monochromatic lights. Or, the light-emitting regions can emit lights having different frequency ranges, and the lights are mixed into the desired light. In FIG. 4B, the anode structures 252 and the cathode structures 254 are, for example, alternately arranged, and the cathode structures 254 are allowed to be used with two anode structures 252 to form two regions. However, only a pair of the anode structure 252 and the cathode structure 254 may also be used, for defining one light-emitting region.

Figure 5:
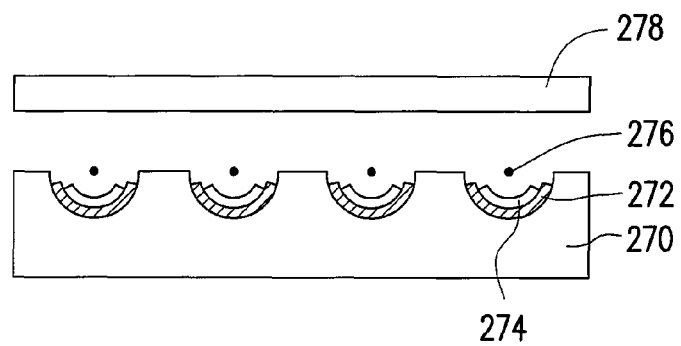
FIG. 5 is a schematic cross-sectional view of a surface light-emitting apparatus according to another embodiment of the present invention.

FIG. 5 is a schematic cross-sectional view of a surface light-emitting apparatus according to another embodiment of the present invention. Referring to FIG. 5, the surface light-emitting apparatus includes a lower substrate 270 and an upper substrate 278, which form the closed space. The substrate may be glass or quartz. In the design of this embodiment, the arrangement of the cathode structure and the anode structure is different from the above embodiments, but the basic mechanism remains unchanged. One or more grooves is/are disposed on the inner surface of the lower substrate 270, the profile of the cross section is a curve, and preferably a circular arc. An anode structure layer 272 and a fluorescent layer 274 are disposed on the surface of the grooves. The cathode structure 276 is, for example, linearly disposed above the groove correspondingly, for example located at a center point of the circular arc. The material of the cathode structure 276 is, for example, metal, carbon nanotube, carbon nanowall, carbon nano material, zinc oxide, or other discharge materials. The anode structure is, for example, a transparent conductive material. The anode structure layer 272 also has the light reflective function. In this manner, the flat light source may be formed by a plurality of anode structure layers 272 and cathode structures 276.

Additionally, if the anode structure layer 272, for example, is metal, the anode structure layer 272 has the reflective function. If the anode structure layer 272, for example, is the conductive transparent material, other changes are allowable. For example, if the voltage of the cathode is a negative potential, the anode may be at the positive potential, for example, a ground potential relative to the negative voltage. Therefore, the lower substrate 270 and the anode structure layer 272 are an integrated metal layer, which has the conductive and reflective function. Here, in the situation of maintaining the required relative voltage difference for keeping the required electric field, if the cathode is at an enough negative potential, the anode may operate at a low voltage, and further, for example, operate at the ground voltage (0 V) instead of high positive voltage. In this manner, the design of the anode structure may be changed or simplified accordingly.

Additionally, if the lower substrate 270 and the anode structure layer 272 are transparent materials, a reflective layer may be disposed on the surface of the grooves, or a total reflective layer is disposed on an outer surface (i.e. the lower surface in the figure) of the lower substrate 270. Other changes will not be exemplified herein. The upper substrate 278 may be a transparent material or a light-reflective material. Further, when the upper substrate 278 and the lower substrate 270 are sealed, the low-pressure gas is maintained. Depending on the sealing manner, the low-pressure gas may be shared or sealed in respective grooves separately. The changes of the detailed design are not limited to the exemplified embodiments.

As described above, the fluorescent layer may be the single layer structure or the multi-layer structure. Since the plurality of light-emitting units are disposed separately, the fluorescent layer may be arranged in an array for respectively emitting different or same color lights, and then mixing the color lights into the light source.

Figure 6A:
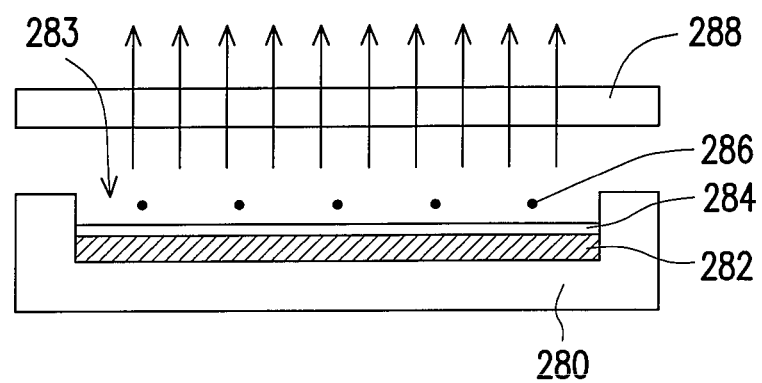
FIGS. 6A and 6B are schematic cross-sectional views of a surface light-emitting apparatus according to other embodiments of the present invention.

FIG. 6A is a schematic cross-sectional view of a surface light-emitting apparatus according to another embodiment of the present invention. Referring to FIG. 6A, this embodiment uses the linear cathode structure 286, which is same as that described above. However, the anode structure layer 282 is a panel disposed on the substrate 280. Preferably, the anode structure layer 282 is disposed in a depressed region 283 of the substrate 280. A fluorescent layer 284 is formed on the anode structure layer 282. The conductive gas is, for example, closed in a space by a substrate 288 and the substrate 280. In this embodiment, the anode structure layer 282 forms a plane, and a plurality of cathode structures 286 is disposed above the anode structure layer 282 so as to form a flat light source.

Hence, according to the desired light-emitting direction, for example, the anode structure layer 282 may have a metal plate having the reflective structure, for reflecting the generated light to the cathode structure 286. In addition, if the anode structure layer 282 is a transparent conductive material, the substrate 280 may have the reflective function, or the reflective layer is added on the other side of the anode structure layer 282. In the design, the light-exit surface of the substrate 288 is formed by a light-transmissive transparent material. In addition, if the substrate 280 is the transparent material, the substrate 288 is designed to be a substrate having the reflective function, for example, a reflector plate or a substrate having a reflective layer, and the light-exit surface is located on the substrate 280. In other words, according to the same light-emitting mechanism, the cathode structure may be a linear design, and the light-exit surface may be determined according to the actual requirements. The reflective structure may be integrated in the light-emitting apparatus at a suitable position, for reflecting light in the desired direction.

Further, with the arrangement of the electrode structure, edges of the substrate 288 and the substrate 280 are, for example, directly sealed by a protruding portion, so as to form the closed space without using additional sidewall structure. The protruding portion of the substrate may be, for example, disposed on one or both of the two substrates 280 and 288.

Figure 6B:
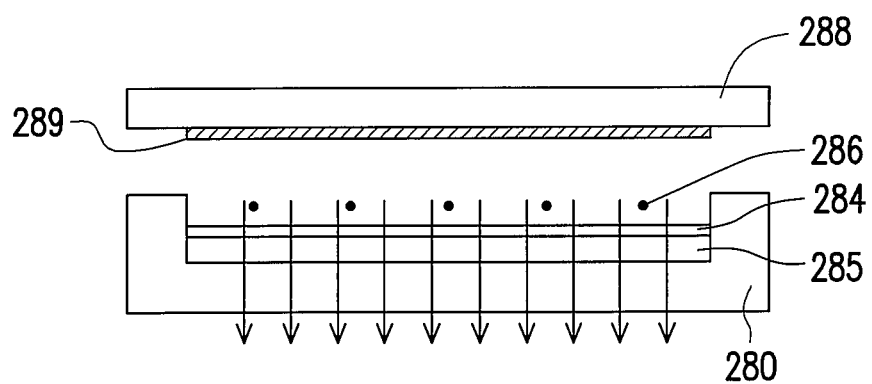

For matching with the substrate 280, the anode structure layer 282 of the embodiment of FIG. 6A is designed to have the light reflective function, so a part of the fluorescent light emitted in the direction towards the anode structure layer 282 may be reflected. Thus, the emitted light is emitted towards the substrate 288. However, in FIG. 6A, other design changes are allowable. For example, FIG. 6B is schematic cross-sectional view of a surface light-emitting apparatus according to another embodiment of the present invention. Referring to 6B, both the anode structure layer 285 and the substrate 280 adopt the light-transmissive material. The anode structure layer 285 is, for example, the transparent conductive oxide. A reflective layer 289 is disposed on the substrate 288. In this manner, a part of the lights emitted from the fluorescent layer 284 may be reflected by the reflective layer 289, and the other part of the lights is emitted in the direction towards the substrate 280. The above description is an illustration of some embodiments of the possible design changes.

Additionally, if the structure of the to-be-inspected device is, for example, the curving surface, the light source apparatus may generate a curving surface light source by the substrate curving surface design, which are one of the actual design changes.

In operation of the light source apparatus, the light-emitting luminance and the operating voltage of the light source apparatus are substantially in a linear relation, thus achieving a continuous dimming. The user can adjust the desired brightness conveniently according to the characteristics of the product. Different light colors can be exhibited by adjusting proportions of the fluorescent powders, thus further meeting the requirements of different product characteristics in inspection.

Figure 7:
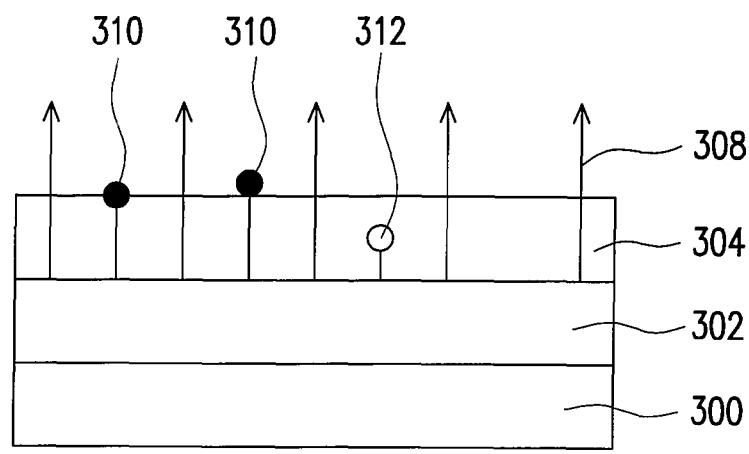
FIG. 7 is a schematic view of a system for inspecting defects of a panel device according to an embodiment of the present invention.

FIG. 7 is a schematic view of a system for inspecting defects of a panel device according to an embodiment of the present invention. Referring to FIG. 7, the basic architecture of the system for inspecting defects of a panel device of the present invention includes a power unit 300, a light source apparatus 302, and a to-be-inspected device 304. The light source apparatus 302 generates an inspection light by the use of the light source apparatus of the above embodiment. In this embodiment, for example, the light source apparatus 302 holds the to-be-inspected device 304, and is controlled by the power unit 300 to provide an inspection light to the to-be-inspected device 304 for inspecting whether or not having defects. Here, the defects are, for example, foreign particles 310 on the surface of the to-be-inspected device 304 or holes 312 inside the to-be-inspected device 304. The intensity of the light 308 generated by the light source apparatus 302 after passing through the to-be-inspected device 304 has changes at the defects, thereby finding the defects.

As described above, the detailed structure of the light source apparatus 302, for example, mainly includes a cathode structure, an anode structure, a fluorescent layer, and a low-pressure gas layer. The fluorescent layer is located between the cathode structure and the anode structure. The low-pressure gas layer is filled between the cathode structure and the anode structure, and has the function of inducing the cathode to emit the electrons uniformly. The low-pressure gas layer has an electron mean free path, allowing at least enough electrons to directly hit the fluorescent layer under an operating voltage.

FIG. 8 is a schematic view of profiles of a light source apparatus and a power unit according to an embodiment of the present invention. Referring to FIG. 8(*a*), the light source apparatus 302 is manufactured by a round substrate. A round light source apparatus may be obtained with the assist of a power unit 300, for generating a surface inspection light. Referring to FIG. 8(*b*), the light source apparatus 302 is manufactured by a quadrangular substrate. A quadrangular light source apparatus may be obtained with the assist of the power unit 300, for generating a quadrangular inspection light. Definitely, other shapes are allowable according to the actual requirements.

FIG. 9 is a schematic view of a system for inspecting defects of a panel device according to an embodiment of the present invention. Referring to FIG. 9, the to-be-inspected device 402 may be inspected in other manners in addition to the manner of FIG. 7. For example, in FIG. 9(*a*), the light source apparatus 400 provides a fixed light source. The to-be-inspected device 402 is disposed on a movable platform 404, for example, a manipulator mechanism for moving the to-be-inspected device 402. On the other hand, an image photographing device 406 observing the inspection light, for example, a charge coupled device (CCD), is used to observe the image passing through the to-be-inspected device 402 at a corresponding position.

Additionally, referring to FIG. 9(*b*), another arrangement manner is shown. If the reflected image of the to-be-inspected device 402 needs inspection, the light source apparatus 400 provides the inspection light from the lateral side, and the image photographing device 406 inspects the reflected image in a corresponding direction. The to-be-inspected device 402 is placed on the moveable platform 408, and is moved by the moveable platform 408.

Further, referring to FIG. 9(*c*), another arrangement manner is shown, which is similar to the manner of FIG. 9(*b*), except that the light source apparatus 400 provides the inspection light from the front side. The image photographing device 406 inspects the reflected image in the corresponding direction at the lateral side. The to-be-inspected device 402 is placed on the moveable platform 408, and is moved by the moveable platform 408.

The to-be-inspected device 402 is held by the platform, such that the inspection is further systematized and automated, which is labor-saving. The arrangement manner of FIG. 9 is only an example. The light source apparatus of the present invention may provide suitable surface inspection light, which is helpful for improving the inspecting efficiency. The light source apparatus generates the inspection light by using the low-pressure gas as the mechanism. The cathode structure and the anode structure may be changed according to the actual requirements.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A system for inspecting defects of a panel device, comprising:
   a to-be-inspected device;
   a power unit; and
   a light source apparatus, holding the to-be-inspected device, wherein a light emitting flat plane of the light source apparatus is directly contacting with the to-be-inspected device, wherein the to-be-inspected device, the power unit, and the light source apparatus are formed as an integrated module, wherein the light source apparatus is controlled by the power unit to provide an inspection light to the to-be-inspected device for inspecting whether or not having defects, wherein the light source apparatus comprises:
   a cathode structure;
   an anode structure;
   a fluorescent layer, located between the cathode structure and the anode structure; and
   a low-pressure gas layer, filled between the cathode structure and the anode structure, for inducing a cathode to emit electrons uniformly, wherein the low-pressure gas layer comprises an electron mean free path, allowing electrons to directly hit the fluorescent layer under an operating voltage.

2. The system for inspecting defects of a panel device according to claim 1, wherein the cathode structure and the anode structure are respectively surface structures in parallel with each other, for providing a surface inspection light.

3. The system for inspecting defects of a panel device according to claim 1, wherein a pressure of the low-pressure gas layer is in a range of $10$-$10^{-3}$ torrs.

4. A system for inspecting defects of a panel device, comprising:
   a to-be-inspected device;
   a platform, holding the to-be-inspected device;
   a power unit; and
   a light source apparatus, controlled by the power unit to provide an inspection light to the to-be-inspected device for inspecting whether or not having defects, wherein a light emitting flat plane of the light source apparatus is directly contacting with the to-be-inspected device, wherein the to-be-inspected device, the power unit, and the light source apparatus are formed as an integrated module, wherein the light source apparatus comprises:
   a cathode structure;
   an anode structure;
   a fluorescent layer, located between the cathode structure and the anode structure; and
   a low-pressure gas layer, filled between the cathode structure and the anode structure, for inducing a cathode to emit electrons uniformly, wherein the low-pressure gas layer comprises an electron mean free path, allowing electrons to directly hit the fluorescent layer under an operating voltage.

5. The system for inspecting defects of a panel device according to claim 4, wherein the cathode structure and the anode structure are respectively surface structures in parallel with each other, for providing a surface inspection light.

6. The system for inspecting defects of a panel device according to claim 4, wherein a pressure of the low-pressure gas layer is in a range of $10$-$10^{-3}$ torrs.

7. The system for inspecting defects of a panel device according to claim 4, further comprising a sidewall structure, for separating the cathode structure and the anode structure to form a closed space for the low-pressure gas layer.

8. The system for inspecting defects of a panel device according to claim 4, wherein the fluorescent layer is located on a surface of the anode structure.

9. The system for inspecting defects of a panel device according to claim 4, wherein the to-be-inspected device is a display panel.

10. The system for inspecting defects of a panel device according to claim 4, wherein the platform moves the to-be-inspected device.

11. The system for inspecting defects of a panel device according to claim 4, further comprising a photographing device for taking photographs of the to-be-inspected device.

12. The system for inspecting defects of a panel device according to claim 4, wherein a surface of the cathode structure and/or the anode structure of the light source apparatus further comprises a discharge material layer.

13. The system for inspecting defects of a panel device according to claim 4, wherein a surface of the cathode structure of the light source apparatus further comprises a secondary electron source material.

14. The system for inspecting defects of a panel device according to claim 4, wherein a gas of the low-pressure gas layer comprises inert gas or atmospheric air.

15. The system for inspecting defects of a panel device according to claim 4, wherein a gas of the low-pressure gas layer comprises $O_2$, $H_2$, or $CO_2$.

16. The system for inspecting defects of a panel device according to claim 4, wherein the fluorescent layer on the anode structure of the light source apparatus emits a visible light according to a selected material.

17. The system for inspecting defects of a panel device according to claim 4, wherein the anode structure of the light source apparatus is a surface structure.

18. The system for inspecting defects of a panel device according to claim 4, wherein the cathode structure of the light source apparatus is a surface structure, and the fluorescent layer is located on a surface of the anode structure facing the cathode structure.

19. The system for inspecting defects of a panel device according to claim 4, wherein the cathode structure of the light source apparatus comprises at least one linear cathode.

20. The system for inspecting defects of a panel device according to claim 4, wherein the light source apparatus further comprises a substrate structure, comprising at least one curved groove, wherein the cathode structure is at least one linear cathode extending above the curved groove, and the anode structure is located on a concave surface of the curved groove.

21. The system for inspecting defects of a panel device according to claim 4, wherein the light source apparatus further comprises:
   a first substrate; and
   a second substrate, forming a closed space with the first substrate,
   wherein the anode structure and the cathode structure are placed on the first substrate in the closed space,
   the fluorescent layer is composed of a plurality of monomers, located between the cathode structure and the anode structure on the first substrate, for forming at least one light-emitting region,
   the low-pressure layer is filled in the closed space, for inducing the cathode to emit electrons uniformly.

22. The system for inspecting defects of a panel device according to claim 4, wherein the to-be-inspected device comprises an image display panel.

* * * * *